US012285458B2

(12) United States Patent
Powell (10) Patent No.: US 12,285,458 B2
(45) Date of Patent: Apr. 29, 2025

(54) COMPOSITIONS AND METHODS FOR ALLEVIATING ADVERSE EFFECTS FROM RESPONSIBLE ALCOHOL CONSUMPTION

(71) Applicant: Cheers Health, Inc., Houston, TX (US)

(72) Inventor: Brooks Powell, Houston, TX (US)

(73) Assignee: Cheers Health, Inc., Houston, TX (US)

( * ) Notice: Subject to any disclaimer, the term of this patent is extended or adjusted under 35 U.S.C. 154(b) by 0 days.

(21) Appl. No.: 18/648,175

(22) Filed: Apr. 26, 2024

(65) Prior Publication Data

US 2024/0358789 A1    Oct. 31, 2024

Related U.S. Application Data

(60) Provisional application No. 63/499,118, filed on Apr. 28, 2023.

(51) Int. Cl.
| | |
|---|---|
| *A61K 36/9068* | (2006.01) |
| *A61K 31/198* | (2006.01) |
| *A61K 31/355* | (2006.01) |
| *A61K 31/375* | (2006.01) |
| *A61K 31/51* | (2006.01) |
| *A61K 31/522* | (2006.01) |
| *A61K 31/675* | (2006.01) |
| *A61K 31/7034* | (2006.01) |
| *A61K 31/714* | (2006.01) |
| *A61K 33/00* | (2006.01) |
| *A61K 36/534* | (2006.01) |
| *A61K 36/76* | (2006.01) |
| *A61K 36/82* | (2006.01) |

(52) U.S. Cl.
CPC ...... *A61K 36/9068* (2013.01); *A61K 31/198* (2013.01); *A61K 31/355* (2013.01); *A61K 31/375* (2013.01); *A61K 31/51* (2013.01); *A61K 31/522* (2013.01); *A61K 31/675* (2013.01); *A61K 31/7034* (2013.01); *A61K 31/714* (2013.01); *A61K 33/00* (2013.01); *A61K 36/534* (2013.01); *A61K 36/76* (2013.01); *A61K 36/82* (2013.01)

(58) Field of Classification Search
None
See application file for complete search history.

(56) References Cited

U.S. PATENT DOCUMENTS

| | | | |
|---|---|---|---|
| 5,759,539 A | 6/1998 | Whitmire | |
| 6,485,758 B2 | 11/2002 | Mirza et al. | |
| 6,827,932 B2 | 12/2004 | Crippen et al. | |
| 9,474,802 B2 | 10/2016 | Burg | |
| 9,603,830 B2 | 3/2017 | Powell | |
| 9,744,202 B2 | 8/2017 | Burg | |
| 9,962,365 B2 | 5/2018 | Powell | |
| 10,398,675 B2 | 9/2019 | Powell | |
| 10,478,416 B1 | 11/2019 | Powell | |
| 10,736,870 B2 | 8/2020 | Powell | |
| 11,504,353 B2 | 11/2022 | Powell | |
| 11,717,507 B2 | 8/2023 | Powell | |
| 2007/0213400 A1* | 9/2007 | Okubo | A61P 3/00 514/561 |
| 2008/0020071 A1* | 1/2008 | Diaz | A61P 25/32 514/467 |
| 2008/0075710 A1* | 3/2008 | Cornett | A61K 31/525 514/276 |
| 2013/0344136 A1* | 12/2013 | Duelo Riu | A61K 31/522 424/94.4 |
| 2015/0305249 A1 | 10/2015 | Miller et al. | |
| 2015/0342923 A1 | 12/2015 | Powell | |
| 2017/0056459 A1* | 3/2017 | Keegan | A61K 31/375 |
| 2017/0246143 A1 | 8/2017 | Powell | |
| 2019/0029995 A1 | 1/2019 | Powell | |
| 2019/0336474 A1 | 11/2019 | Powell | |
| 2020/0016117 A1 | 1/2020 | Powell | |
| 2020/0147032 A1 | 5/2020 | Prud'Homme et al. | |
| 2020/0197364 A1 | 6/2020 | Prud'Homme et al. | |
| 2020/0215027 A1 | 7/2020 | Prud'Homme et al. | |
| 2020/0330426 A1 | 10/2020 | Powell | |
| 2022/0062223 A1 | 3/2022 | Prud'Homme et al. | |
| 2022/0202768 A1 | 6/2022 | Prud'Homme et al. | |
| 2022/0265600 A1 | 8/2022 | Powell et al. | |

(Continued)

FOREIGN PATENT DOCUMENTS

| | | |
|---|---|---|
| WO | 2012058589 A1 | 5/2012 |
| WO | 2019050969 A1 | 3/2019 |

(Continued)

OTHER PUBLICATIONS

"BluCetin Liver and Immune Support", http://www.blucetin.com, downloaded Oct. 1, 2015, Oct. 1, 2015, 4 pages.
"Cheers Hydrate," retrieved from the internet Aug. 28, 2024, https://cheershealth.com/products/hydrate, 5 pages.
"Cheers Multi," retrieved from the internet Aug. 28, 2024, https://cheershealth.com/products/multi, 6 pages.
"Cheers Protect," retrieved from the internet Aug. 28, 2024, https://cheershealth.com/products/protect, 6 pages.
"Cheers Relief," retrieved from the internet Aug. 28, 2024, https://cheershealth.com/products/relief, 6 pages.

(Continued)

*Primary Examiner* — Susan Hoffman
(74) *Attorney, Agent, or Firm* — Perkins Coie LLP (57) ABSTRACT

Disclosed are compositions for alleviation from adverse physical effects and symptoms of responsible alcohol consumption, and methods for manufacturing and/or administering the compositions. In some aspects, a composition to alleviate discomforting symptoms associated with responsible alcohol consumption includes various formulations of ginger root, L-Theanine, and/or caffeine, which may be derived from particular ingredient sources. In some embodiments, the composition(s) may optionally include salicin. In some embodiments, the composition(s) may optionally include a blend of particular vitamins, electrolytes, and/or salts.

5 Claims, 3 Drawing Sheets

(56) References Cited

U.S. PATENT DOCUMENTS

| | | | |
|---|---|---|---|
| 2023/0089539 | A1 | 3/2023 | Powell |
| 2023/0210812 | A1 | 7/2023 | Prud'Homme et al. |
| 2023/0285352 | A1 | 9/2023 | Prud'homme et al. |
| 2023/0338332 | A1 | 10/2023 | Powell |
| 2024/0261254 | A1 | 8/2024 | Prud'Homme et al. |

FOREIGN PATENT DOCUMENTS

| | | | |
|---|---|---|---|
| WO | 2020099937 | A2 | 5/2020 |
| WO | 2020252346 | A1 | 12/2020 |
| WO | 2024167506 | A1 | 8/2024 |
| WO | 2024167593 | A1 | 8/2024 |

OTHER PUBLICATIONS

"Cheers Restore," retrieved from the internet Aug. 28, 2024, https://cheershealth.com/products/restore, 5 pages.

"Founder of Cheers discusses his Shark Tank appearance," Closer's Coffee, retrieved from the internet Aug. 28, 2024, https://youtube.com/watch?v=LygBHIPmpyg.

"Meet Cheers = Leader in Alcohol-Related Health," Cheers, retrieved from the internet Aug. 28, 2024, https://www.youtube.com/watch?v=NLgzSaTK91k.

"Alcohol Beverages Market Size, Share & Industry Analysis, By Type (Beer, Wine, Distilled Spirits, and Others), By Distribution Channel (Retail and Food Services), and Regional Forecast, 2024-2032," Fortune Business Insights, Apr. 23, 2024.

Ling et al. "Cognitive and psychomotor performance during alcohol hangover," Current Drug Abuse Review, 2010, 3(2):80-87.

Juneja et al. "L-theanine—a unique amino acid of green tea and its relaxation effect in humans," Trends in Food Science & Technology, 1999, 10:199-204.

Ramadhanu et al. "Effectiveness of Ginger in Treating Nausea and Vomiting of Pregnancy," Eureka Herba Indonesia, 2022, 3(1):111-115.

Ryan et al. "Ginger," Oncology Nurse Edition, Feb. 2010, 24(2):46-49.

Swift et al. "Alcohol Hangover: Mechanisms and Mediators," Alcohol Health & Research World, 1998, 22(1):54-60.

Ternay et al. "Therapeutic Prospects of Cannabidiol for Alcohol Use Disorder and Alcohol-Related Damages on the Liver and the Brain," Frontiers in Pharmacology, May 31, 2019 10(627):1-11.

Vlachojannis et al. "Willow Species and Aspirin: Different Mechanism of Actions," Phytotherapy Research, 2011.

Atkuri, Kondala R., et al., "N-acetylcysteine—a safe antidote for cysteine/glutathione deficiency," Curr Opin Pharmacol. 7(4): 355-359, 2007.

Gould, Rebecca L., et al., "Impact of Supplementary Amino Acids, Micronutrients, and Overall Diet on Glutathione Homeostasis," Nutrients, 11, 1056, p. 1-21, 2019.

Millea, Paul J., et al., "N-Acetylcysteine: Multiple Clinical Applications," American Family Physician vol. 80, No. 3, p. 265-269, 2009.

Pedre, Brandan, et al., "The mechanism of action of N-acetylcysteine (NAC): The emerging role of H2S and sulfane sulfur species," Pharmacology & Therapeutics 228, 107916, 2021.

Plaza, Noelia Clemente, et al., "Effects of the Usage of L-Cysteine (L-Cys) on Human Health," Molecules, 23, 575, p. 1-13, 2018.

Sansone, Randy, A., et al., "Getting a knack for NAC: N-Acetyl-Cysteine," Innov Clin Neurosci. 8(1): p. 10-14, 2011.

Schmitt, Bernard, et al., "Effects of N-acetylcysteine, oral glutathione (GSH) and a novel sublingual form of GSH on oxidative stress markers: A comparative crossover study," Redox Biology 6, p. 198-205, 2015.

"AfterPartyPalTM", http://afterpartypal.com, downloaded Sep. 29, 2015, Sep. 29, 2015, 7 pages.

"Berocca", http://buyberocca.com/en/home/, downloaded Oct. 6, 2015, Oct. 6, 2015, 3 pages.

"Blowfish for Hangovers", http://forhangovers.com/, downloaded Oct. 6, 2015, Oct. 6, 2015, 3 pages.

"Bytox", https://www.bytox.com/, downloaded Oct. 6, 2015, Oct. 6, 2015, 1 page.

"Chaser", http://www.consumersearch.com/as-seen-on-tv/chaser, downloaded Oct. 6, 2015, Oct. 6, 2015, 3 pages.

"Dihydromyricetin Depot", http://dhmdepot.com, downloaded Sep. 29, 2015, Sep. 29, 2015, 9 pages.

"Dr. P's HG3 Hangover Prevention Tablet", http://www.drphg3.com, downloaded Sep. 29, 2015, Sep. 29, 2015, 5 pages.

"Drink Ease", http://www.drinkease.com/, downloaded Oct. 6, 2015, Oct. 6, 2015, 2 pages.

"Drinkin Mate Drinkin' Mate Feel Better the Next Day", eVitamins.com, http://www.evitamins.com/drinkin-mate-feelbetter--drinkin-mate-14871 downloaded Sep. 9, 2015, Sep. 9, 2015, 3 pages.

"Drinkwel", http://www.drinkwel.com, downloaded Oct. 1, 2015, Oct. 1, 2015, 1 page.

"Forget Hangovers", http://forgethangovers.com/, downloaded Oct. 6, 2015, Oct. 6, 2015, 2 pages.

"GTOX Detox & Recovery Shot", https://www.facebook.com/GTOXNOW, downloaded Sep. 29, 2015, Sep. 29, 2015, 8 pages.

"Hangover Destroyer", http://hdestroyer.com/, downloaded Oct. 6, 2015, Oct. 6, 2015, 6 pages.

"Hangover Guardian: Advanced Hangover Pills", http://www.amazon.com/Hangover-Guardian-Advanced-Activated-Charcoal/dp/B00BD5KOFG, downloaded Oct. 6, 2015, Oct. 6, 2015, 7 pages.

"Hangover Salvation", http://hangoversalvation.com/, downloaded Oct. 6, 2015, Oct. 6, 2015, 4 pages.

"HangoverStopper", http://www.hangoverstopper.com/?gclid=CPqO-SKNicYCFQGnaQodYnlAuA, downloaded Oct. 6, 2015,, Oct. 6, 2015, 2 pages.

"Hang-Zen", http://drinkhangzen.com, downloaded Oct. 1, 2015, Oct. 1, 2015, 2 pages.

"Happy Hour Vitamins", http://happyhourvitamins.com/, downloaded Oct. 6, 2015, Oct. 6, 2015, 12 pages.

"Küre Hangover Prevention and Recovery", http://www.amazon.com/KÜRE-Prevention-Recovery-Satisfaction-Guarantee/dp/B00H4FZQ51, downloaded Oct. 6, 2015, Oct. 6, 2015, 7 pages.

"Life Support", https://lifesupport.com, downloaded Oct. 1, 2015, Oct. 1, 2015, 5 pages.

"LifeExtension® Anti-Alcohol Antioxidants with HepatoProtection Complex", http://www.lifeextension.com/vitaminssupplements/Item01440/Anti-Alcohol-Antioxidants-with-HepatoProtection-Complex, downloaded Oct. 6, 2015, Oct. 6, 2015, 9 pages.

"Mercy Nutraceuticals, Inc.", http://webstore.drinkmercy.com, downloaded Oct. 1, 2015, Oct. 1, 2015, 1 page.

"Never Too Hungover", http://nevertoohungover.com/, downloaded Oct. 1, 2015, Oct. 1, 2015, 8 pages.

"No-Hang", http://www.nightlifesupplements.com/we-found-a-better-mousetrap-no-hang/, downloaded Oct. 6, 2015, Oct. 6, 2015, 3 pages.

"NOHO Drink", http://www.nohodrink.com/, downloaded Oct. 6, 2015, Oct. 6, 2015, 2 pages.

"PartySmart®", http://www.partysmart.net/in/flash/stage.html, downloaded Oct. 6, 2015, Oct. 6, 2015, 1 page.

"Pre|game", http://getpregame.com, downloaded Oct. 1, 2015, Oct. 1, 2015, 7 pages.

"PreToxx for Hangovers & Lover Support", http://www.amazon.com/Hangovers-Vegetarian-Capsules-Electrolyte-Guarantee/dp/B001EM7T34, downloaded Sep. 29, 2015, Sep. 29, 2015, 7 pages.

"Previtalise", https://www.facebook.com/previtalise, downloaded Oct. 6, 2015, Oct. 6, 2015, 4 pages.

"Rally Capsules", http://www.rallycapsules.com/, downloaded Oct. 6, 2015, Oct. 6, 2015, 10 pages.

"RU21 Hangover Pill", http://www.ru21.com/, downloaded Oct. 1, 2015, Oct. 1, 2015, 5 pages.

"Sobur Hangover Pills", http://www.sobur.co/, downloaded Oct. 6, 2015, Oct. 6, 2015, 8 pages.

"Source Naturals Hangover FormulaTM", http://www.sourcenaturals.com/products/GP1149, downloaded Oct. 1, 2015, Oct. 1, 2015, 1 page.

"Texas Hangover Cure", http://www.texashangovercure.com/, downloaded Oct. 6, 2015, Oct. 6, 2015, 1 page.

"The Hangover Recovery Shot", http://www.hangoverjoes.com/index.php, downloaded Oct. 1, 2015, Oct. 1, 2015, 4 pages.

(56) References Cited

OTHER PUBLICATIONS

"Toniiq", http://www.toniiq.com/, downloaded Oct. 6, 2015, Oct. 6, 2015, 5 pages.
"Trendmonitor", http://trndmonitor.com/product-spotlight-lastcall-productivity-beverage/, downloaded Oct. 1, 2015, Oct. 1, 2015, 2 pages.
"Zaca®", http://www.zacalife.com, downloaded Oct. 1, 2015, Oct. 1, 2015, 3 pages.
Braun, S , "Buzz", The Science and Lore of Alcohol and Caffeine, 1997, pp. 82-86.
Howland, Jonathan , et al., "Hangover Predicts Residual Alcohol Effects on Psychomotor Vigilance the Morning After", Journal of Addiction Research Therapy, 2010; 1(101), 11 pages.
Rohsenow, Damaris J, et al., "The Acute Hangover Scale: A new measure of immediate hangover symptoms", Addictive Behaviors, 2007, 32(6):1314-20, Jun. 2007.
Shen, Yi , et al., "Dihydromyricetin as a novel anti-alcohol intoxication medication", J. Neurosci, 2012, 32(1):390-401.
Wechsler, Henry Ph.D., et al., "Health and behavioral consequences of binge drinking in college. A national survey of students", JAMA, 1994, 272: 1672-77, 1994, 1672-77.
Wiese, Jefffrey G, et al., "The alcohol hangover", Annals of Internal Medicine, 2000; 132(11), Jun. 6, 2000, 897-902.

\* cited by examiner

COMPOSITIONS AND METHODS FOR ALLEVIATING ADVERSE EFFECTS FROM RESPONSIBLE ALCOHOL CONSUMPTION

CROSS-REFERENCE TO RELATED APPLICATIONS

This patent document claims priority to and the benefits of U.S. Provisional Patent Application No. 63/499,118, filed on Apr. 28, 2023. The entire contents of the afore-mentioned patent application are incorporated by reference as part of the disclosure of this application.

TECHNICAL FIELD

This patent document relates to compositions and methods for relieving side effects of responsible alcohol consumption.

BACKGROUND

Alcohol is a constituent of medicines, foods, and beverages that produces both beneficial and detrimental effects on human beings. Alcohol typically refers to ethyl alcohol (ethanol), which is the common form of consumable alcohol found in alcoholic beverages such as, e.g., beer, wine, and liquor. Consumable alcohol is produced by fermentation processes of various food products, e.g., including wheat, rice, or other starches, fruits, honey, or other sources of sugars, and yeast. In the United States, the National Institute on Alcohol Abuse and Alcoholism (NIAAA) of the National Institutes of Health (NIH) considers a standard drink to be equal to 0.6 ounces of pure ethanol, which is equivalent to approximately 12 fluid ounces (fl. oz.) of regular beer (of about 5% alcohol), 8-9 fl. oz. of malt liquor (of about 7% alcohol), 5 fl. oz. of wine (of about 12% alcohol), and 1.5 fl. oz. (referred to as a "shot") of an 80-proof distilled spirit or liquor (e.g., gin, rum, vodka, whiskey, tequila, etc.).

During consumption, alcohol is rapidly absorbed from the stomach and small intestine into the bloodstream, from which it can affect several organs including the brain, heart, pancreas, and liver. Alcohol can act as a depressant to the central nervous system (CNS). For example, alcohol interferes with the brain's communication pathways, which affects brain functionality in a way that manifests in cognitive and behavioral changes, such as a person's mood and behavior as well as his/her ability to think, focus, and move. Alcohol can cause inflammation and damage to the liver, e.g., to the extent where consistent heavy drinking can cause chronic liver problems. For example, heavy drinking can lead to steatosis (e.g., or fatty liver), infection (e.g., alcoholic hepatitis), fibrosis, and cirrhosis.

SUMMARY

Disclosed are compositions and methods for promoting recovery from adverse side effects of responsible alcohol consumption by a consumer of alcohol ("consumer"). In some aspects, a composition for alleviating adverse effects (e.g., relieving discomforting symptoms) associated with responsible alcohol consumption by a consumer and/or restoring and/or stimulating production of vital biochemicals (e.g., metabolites, enzymes) of the consumer is contained in a delivery unit, e.g., including but not limited to one or more capsule(s), tablet(s), powder(s), liquid(s), gummy(ies), chewable tablet(s), gum(s), lozenge(s), infused food(s), or other solid form that can be ingested by the consumer to promote the consumer's recovery from detrimental physical effects of the responsible alcohol consumption. In some embodiments, the composition includes one or more of ginger, L-Theanine, and/or caffeine; and in some embodiments, the composition may optionally include salicin and/or hemp-derived cannabidiol. In some aspects, a method for administering the composition contained in the capsule, tablet, powder, liquid, gummy, chewable tablet, gum, lozenge, infused food, or other solid form includes formulating the composition and providing a dosage of the composition in the delivery unit to be consumed after a period of time after responsible alcohol consumption by the consumer.

In some embodiments, for example, a composition for mitigating adverse effects of alcohol (e.g., responsible alcohol consumption by a person) may include various formulations of ginger, L-Theanine, caffeine, and/or salicin, which may be derived from particular ingredient sources. For example, in some embodiment of the composition including ginger, the ginger may be derived from ginger root (*Zingiber officinale*). For example, in some embodiments of the composition including L-Theanine, the L-Theanine, may be derived from Green Tea (*Camellia sinensis*) (leaf) Extract. For example, in some embodiments of the composition including caffeine, the caffeine may be derived from Green Tea (*Camellia sinensis*) (leaf) Extract. For example, in some embodiment of the composition including salicin, the salicin may be derived from White Willow (*Salix alba*) Bark Extract. In some embodiments, for example, the composition may include a blend of particular vitamins, minerals, electrolytes and salts.

In some embodiments in accordance with the present technology, an ingestible substance includes a composition for mitigating adverse effects of responsible alcohol consumption by a person, which may include ginger, L-Theanine, and caffeine, where the ingestible substance includes at least one of a capsule, tablet, powder, liquid, gummy, chewable tablet, gum, lozenge, infused food, or other solid structure or liquid medium. In some embodiments in accordance with the present technology, a method for mitigating adverse effects of responsible alcohol consumption includes formulating a composition that comprises ginger, L-Theanine, and caffeine (and, optionally, salicin and/or one or more B vitamins and/or Vitamin C), and providing a dosage of the composition to be consumed during a period of time after responsible alcohol consumption by a consumer.

The subject matter described in this patent document can be implemented in specific ways that provide one or more of the following features. For example, the disclosed compositions include formulations of ingredients capable of effectively and comprehensively addressing multiple adverse, detrimental, and/or discomforting symptoms and negative effects of responsible alcohol consumption. In some implementations, for example, compositions of the present technology can be used as a daily supplement to aid in the replenishing of nutrients and electrolytes of the individual, to induce a feeling of an energy boost to the individual, and/or to reverse feelings of nausea or drowsiness of the individual.

DETAILED DESCRIPTION

The ingestion of alcohol (i.e., ethanol) has numerous effects on the human brain and body. The immediate effect of alcohol on humans is that of intoxication. This varies in degrees based on the tolerance of the individual and the number of drinks consumed as well as the amount of different types of food and beverages consumed prior to drinking.

The alcohol is transmitted throughout the body via the bloodstream and is progressively cleared from the blood primarily via the liver. Once alcohol has been cleared from the bloodstream, individuals may experience one or more of an array of discomforting physical symptoms that affect a person shortly after responsibly ingesting alcohol, e.g., within hours of consumption. These discomforting symptoms may include, for example, one or more of thirst, fatigue and/or weakness, headache and/or muscle aches, dizziness/faintness, loss of appetite, poor and/or decreased sleep, nausea and/or stomach pain (e.g., which can include vomiting), and elevated heart rate.

Adverse side effect of responsible alcohol consumption on the consumer can vary based on characteristics of the individual (e.g., body mass, age, hydration level, etc.), amount of alcohol ingested, and other ingredients, foods, or liquids consumed before, during, or after the responsible alcohol consumption. Despite the variability of parameters that affect the degree to which discomforting symptoms are felt by an individual, the adverse side effect occurs in an individual even if he or she does not have significant visible symptoms, as the body has undergone the negative physical effects of alcohol even if the user is not consciously aware of it.

The present technology addresses problems associated with the adverse side effects and discomforting symptoms by responsible alcohol consumption, including addressing significant perceptible symptoms consciously felt by the responsible alcohol consumer and also physical effects of the alcohol on the body that may not be consciously experienced.

Disclosed are compositions, articles, and methods to promote relief and/or recovery from adverse effects of responsible alcohol consumption.

Usually alcohol is consumed through "alcoholic beverages." Alcoholic beverages are drinks that contain the molecule ethanol. Ethanol is the primary psychoactive ingredient in alcoholic beverages, e.g., including wine, beer, and distilled spirits. In the United States, for example, according to the NIAAA approximately 86% of Americans 18 or older reported that they have consumed alcoholic beverages at some point in their lifetime, with over 50% reporting that they have drank in the past month. Owing to the popularity of alcoholic beverages, alcohol can be considered one of the most popular substances in the world. According to the U.S. Beverage Alcohol Forum, for 2012, the U.S. market size of alcoholic beverages was $197.8 billion in retail sales dollars. According to Fortune Business Insights, the U.S. market size for alcoholic beverages was valued at $2.313 trillion and projected to grow over ten percent over the next eight years.

Because responsible alcohol consumption can result in physically detrimental symptoms such as lethargy, headaches, nausea, and other symptoms, it often reduces a person's ability to work at their normal or desired state. For example, a study of college students found that 25% had experienced negative effects of alcohol in the previous week, and 29% reported losing school time for symptom recovery (e.g., Wiese et al., Annals of Internal Medicine 132 (11): 897-902, June 2000). Individuals who have responsibly consumed alcohol and experience detrimental symptoms the following day (e.g., at times of day proximate to their work schedule) can cause economic losses. For example, it was estimated that $3.3 billion in lost U.S. wages occur each year as a result of work missed because of adverse effects of responsible alcohol consumption suffered by employees (e.g., Ling et al., Current drug abuse reviews 3 (2): 80-7, 2010). Similar results were shown for other countries, including Canada and Finland. Moreover, even if one does go to work while experiencing discomforting symptoms of responsible alcohol consumption, it has been noted that the severity of the perceived symptoms and neurocognitive performance are significantly correlated (e.g., Howland et al., Journal of Addiction Research Therapy (01), January 2010).

In a study reviewing negative effects of alcohol, the physiological factors contributing to a subjects' discomforting feelings were identified as (1) dehydration and electrolyte imbalances, (2) gastrointestinal disturbances, (3) low blood sugar, (4) disruption of sleep and other biological rhythms, (5) headaches, (6) effects of alcohol withdrawal (AW), e.g., including irritability, anxiety, etc., and (7) toxic effects of acetaldehyde and congeners (e.g., Swift and Davidson, Alcohol Health Res. World, 22: 54-60, 1998). It has been shown by Wiese et al. that supplementation with B vitamins can decrease the severity of discomfort felt after alcohol consumption, implying that another cause of discomforting symptoms can be due to (8) vitamin loss. The brain is highly dependent on B vitamins, and a lack of nutrition causes physiological problems.

Acetaldehyde ($CH_3CHO$, also referred to as ethanal) is an aldehyde that is found in nature and also produced by the partial oxidation of ethanol in the liver by an enzyme alcohol dehydrogenase (ADH). Acetaldehyde is considered to be a contributing constituent that causes adverse side effect from alcohol consumption.

The liver acts to clear alcohol and acetaldehyde from the body. Alcohol consumption (and particularly overconsumption) leads to liver stress and L-Glutathione depletion, leaving the individual with a temporarily overtaxed liver that cannot properly clear the body of toxins for a period of time during and after drinking. This over taxation of the liver can lead to a buildup of lactic acid, which is known to be related to feelings of lethargy, e.g., and is thereby also considered to be another physiological factor contributing to discomforting symptoms perceived by the consumer: (9) reduced or impaired liver function in regard to added stress of alcohol on regular liver function.

The present technology is designed to target these nine exemplary physiological factors in a comprehensive way. Moreover, the present technology is designed to reduce physically manifested effects (i.e., the discomforting symptoms felt) after their onset due to responsible alcohol consumption.

Despite an increasing number of anti-alcohol effect products or approaches available, present morning-after products fail to provide the responsible alcohol consumer with an effective composition and/or methodology that is capable of countering all, or at least most, of the known causes of discomforting symptoms and adverse physical and physiological effects of responsible alcohol drinking. Thus, existing products are thereby ineffective at relieving the consumer from their perceived discomforting symptoms or extensively improving the ability to of their body to physically recover. Although some existing products may be considered to be partially effective, there is still a need for a comprehensive solution that addresses a greater number, if not all, of contributing factors that cause the discomforting symptoms and adverse side effects after responsible alcohol consumption. Existing products provide noncomprehensive or incomplete solutions that fail to identify or affect the full spectrum of causes and fail to provide a comprehensive agent to alleviate the negative effects of responsible alcohol consumption. Accordingly, the negative consequences of responsible alcohol consumption continue to impair responsible alcohol consumers globally, which has been shown to affect health and economies as discussed above.

The disclosed technology provides engineered compositions, formulations, delivery systems (e.g., capsules, tablets, powders, liquids, gummies, chewable tablets, gum, infused food, lozenges), and methods for comprehensively treating discomforting symptoms and adverse effects after responsible alcohol consumption that target the full spectrum of causes of such discomforting symptoms and adverse effects and provide more effective relief to persons responsibly consuming alcohol.

EXEMPLARY EMBODIMENTS

Various exemplary embodiments of the disclosed technology are illustrated in the following description and examples. In some embodiments, for example, a composition mitigating adverse effects of alcohol (e.g., responsible alcohol consumption by a person), in accordance with the present technology, includes one or more of ginger (e.g., ginger root, including gingerol and/or shogaol), L-Theanine, and/or caffeine. In some embodiments, for example, a composition of the present technology includes one or more of ginger (e.g., ginger root, including gingerol and/or shogaol), L-Theanine, caffeine, and/or salicin. In some embodiments, for example, a composition of the present technology includes one or more of ginger (e.g., ginger root, including gingerol and/or shogaol), L-Theanine, caffeine, salicin, and/or one or more of vitamin C, vitamin E, vitamin B1, vitamin B6, and vitamin B12. In some embodiments, for example, a composition of the present technology includes one or more of ginger (e.g., ginger root, including gingerol and/or shogaol), L-Theanine, caffeine, and/or one or more of vitamin C, vitamin E, vitamin B1, vitamin B6, and vitamin B12.

Ginger root includes rhizomes (e.g., including gingerol [(S)-5-hydroxy-1-(4-hydroxy-3-methoxyphenyl)-3-decanone] and/or (6)-Shogaol [(E)-1-(4-Hydroxy-3-methoxyphenyl)dec-4-en-3-one]) and/or another of ginger's various constituents (which may be basic in pH) that combat gastrointestinal disturbances, i.e., the second physiological factor discussed above. Ginger root is natural source of ginger that can alleviate nausea and pain as well as act as an anti-inflammatory ingredient which helps to break down alcohol and detoxify the body. In particular, a dosage of about 1000 mg of ginger is capable of relieving sensation of nausea (e.g., in instances of motion sickness). The ginger rhizome can be extracted from ginger root (e.g., Zingiber). Ginger is able to alleviate discomfort through direct interaction with digestive function, avoiding nervous system side effects common to pharmacological substances like dimenhydrinate (e.g., Dramamine®) known to treat nausea, vomiting, and dizziness.

L-Theanine is an amino acid that can be extracted from green and black tea and some mushrooms. L-Theanine is understood to alleviate anxiety caused by an excess of anxiety-inducing neurotransmitter glutamate in the brain. L-Theanine does this by increasing α-waves in the brain (e.g., occipital and parietal regions), as shown by human studies. L-Theanine has been shown in animal models to reach the brain quickly (e.g., within 30 min in rat models) without any metabolic change.

Caffeine is a naturally occurring central nervous system (CNS) stimulant generally extracted from coffee beans. Caffeine is understood to increase breathing and heart rate, thereby increasing the sensation of mental alertness and physical energy. Caffeine can alleviate the sensation of fatigue. Caffeine can act as a vasoconstrictor (e.g., to narrow blood vessels to restrict blood flow) to alleviate pain. Caffeine can also reduce pain through its effects on adenosine receptors that play a role in pain signaling. However, while caffeine has many beneficial effects, caffeine can also raise blood pressure and induce anxiety and jitters.

Yet, caffeine in combination with L-Theanine can reduce the anxiety and jitters effect while maintaining the positive effects of pain relief, sensation of alertness, and boosting physical energy. For instance, L-Theanine acts antagonistically against effects induced by caffeine without thwarting caffeine while adding other benefits such as affecting the release or reduction of neurotransmitters like dopamine and serotonin.

The disclosed technology includes a formulated combination of ginger, L-Theanine, and caffeine that can thereby provide relief for discomforting symptoms after responsible alcohol consumption (e.g., the morning after responsible alcohol consumption). The combination of ginger, L-Theanine, and caffeine can, for example, reduce sensation of restlessness and anxiousness while stimulating alertness, alleviate dizziness/faintness, and sooth the stomach and reduce nausea.

In some implementations of the composition that includes ginger, L-Theanine, and caffeine, for example, the amount of ginger (e.g., ginger root) can be in a range 100 mg to 2000 mg, 250 mg to 1750 mg, 500 mg to 1500 mg, 750 mg to 1250 mg, 900 mg to 1100 mg, 500 mg to 750 mg, 750 mg to 1000 mg, 1000 mg to 1250 mg, or 1250 mg to 1500 mg. In some implementations, the amount of ginger (e.g., ginger root) is 1000 mg. In some implementations of the composition that includes ginger, L-Theanine, and caffeine, for example, the amount of L-Theanine can be in a range 10 mg to 400 mg, 25 mg to 350, 50 mg to 300 mg, 50 mg to 250 mg, 50 mg to 200 mg, 75 mg to 175 mg, 75 mg to 125 mg, 125 mg to 175 mg, or 150 mg to 175 mg. In some implementations, the amount of L-Theanine is 100 mg. In some implementations, the amount of L-Theanine is 162.5 mg. In some implementations of the composition that includes ginger, L-Theanine, and caffeine, for example, the amount of caffeine can be in a range 10 mg to 300 mg, 20 mg to 250 mg, 25 mg to 200 mg, 25 mg to 150 mg, 25 mg to 100 mg, 25 mg to 75 mg, 50 mg to 200 mg, 50 mg to 150 mg, or 100 mg to 150 mg. In some implementations, the amount of caffeine is 50 mg. In some implementations, for example, the amount of caffeine is 130 mg. The amount of ingredients in the compound listed herein can correspond to an amount of ingredients in the compound in a single dose (e.g., a serving dose). The serving dose can include one or more delivery units. For example, in some implementations, one serving dose of the compound corresponds to three delivery units (e.g., three capsules).

In some implementations of the composition, for example, in a composition including ginger, L-Theanine, and caffeine, the amount of ginger (e.g., ginger root) can be 40 wt. % to 80 wt. %, 50 wt. % to 70 wt. %, or 55 wt. % to 60 wt. % (e.g., about 57 wt. %); the amount of L-Theanine can be 2.5 wt. % to 15 wt. %, 5 wt. % to 10 wt. %, 5 wt. % to 7 wt. %, or 7.5 wt. % to 12.5 wt. % (e.g., about 6 wt. % or about 10 wt. %); and the amount of caffeine can be 1 wt. % to 10 wt. %, 1 wt. % to 5 wt. %, or 5 wt. % to 10 wt. % (e.g., about 3 wt. % or about 8 wt. %). In some implementations of the composition, for example, in a composition including ginger root, L-Theanine, and caffeine, the amount of ginger (e.g., ginger root) can be 30 wt. % to 80 wt. %, 40 wt. % to 70 wt. %, or 50 wt. % to 60 wt. % (e.g., about 55 wt. %); the amount of L-Theanine can be 0.5 wt. % to 35 wt. %, 2.5 wt. % to 30 wt. %, 5 wt. % to 25 wt. %, 7.5 wt. % to 20 wt. %, or 10 wt. % to 15 wt. % (e.g., about 6 wt. % or about 12 wt. % or 35 wt. %); and the amount of caffeine can be 0.5 wt. % to 20 wt. %, 1 wt. % to 15 wt. %, 2.5 wt. % to 10 wt. %, or 5 wt. % to 7.5 wt. % (e.g., about 3 wt. % or about 7 wt. % or about 15 wt. %).

The composition can be incorporated into any of a variety of delivery systems, e.g., such as a capsule, liquid, powder, a tablet, a gummy, a chewable tablet, a gum, a lozenge, infused food, or other solid form. In an example of a capsule (e.g., gelatin capsule or vegetarian capsule, such as a cellulose capsule) containing a 580 mg dose of the exemplary composition, the capsule can contain about 333 mg of ginger (e.g., ginger root), about 33 mg of L-Theanine, and about 17 mg of caffeine, e.g., with the remaining mass including optional active ingredients (e.g., salicin, vitamins, and/or electrolytes) or inactive substances. In another example of a capsule containing a 1740 mg dose of the exemplary composition, the capsule can contain about 1000 mg of ginger root, about 100 mg of L-Theanine, and about 50 mg of caffeine e.g., with the remaining mass including optional active ingredients or inactive substances. For example, the gelatin capsule can contain non-active ingredients adding to the mass of the composition's delivery system while not affecting the functionality of the composition. In some examples, a single 00size gelatin capsule can include non-active ingredients including gelatin, microcrystalline, cellulose, magnesium stearate, and food coloring to make capsule colors. In some examples, a single 00size vegetarian capsule can include non-active ingredients including at least one of cellulose, magnesium stearate, and/or silicon oxide, and/or food coloring to make capsule colors. In some implementations of the exemplary composition, for example, three 00size gelatin capsules each containing 30 mg of ginger (e.g., ginger root), 33 mg of L-Theanine, and 17 mg of caffeine may constitute a single dose of the composition.

In some embodiments of the composition, for example, the composition including ginger, L-Theanine, and caffeine can further include salicin (e.g., *Salix alba*). Salicin can be extracted from white willow bark in high purity. Salicin converts to salicylic acid in the human body; salicylic acid is a principal metabolite of aspirin and shares many properties with aspirin and can be therefore considered a natural substitute for aspirin. For example, 1 g of salicin has a pain relief effect comparable to 620 mg of aspirin. Salicin is understood to alleviate pain such as headache and/or body pain.

The disclosed technology includes a formulated combination of ginger, L-Theanine, caffeine, and salicin that can thereby provide relief for discomforting symptoms associated with responsible alcohol consumption (e.g., the morning after responsible alcohol consumption). The combination of ginger, L-Theanine, caffeine, and salicin can, for example, reduce sensation of restlessness and anxiousness while stimulating alertness, alleviate discomfort head and muscle discomfort (e.g., headache and body ache), alleviate dizziness/faintness, and sooth the stomach and reduce nausea.

In some implementations of the composition including ginger, L-Theanine, caffeine, and salicin, for example, the salicin can be included in an amount of at least 50 mg, at least 100 mg, at least 200 mg, at least 300 mg, at least 400 mg, or at least 500 mg. In some implementations of the composition, for example, the amount of salicin can be in a range 50 mg to 3000 mg, 100 mg to 2500 mg, 100 mg to 2000 mg, 100 mg to 1500 mg, 150 mg to 1000 mg, 200 mg to 1000 mg, 200 mg to 800 mg, 300 mg to 700 mg, 400 mg to 600 mg, or 450 mg to 550 mg. In some implementations, the amount of salicin is 500 mg (e.g., per single dose). In some implementations, the amount of salicin in the composition can be 10 wt. % to 50 wt. %, 20 wt. % to 40 wt. %, or 20 wt. % to 30 wt. %. In some implementations, the amount of salicin is about 30 wt. %. In some implementations, the amount of salicin in the composition can be 5 wt. % to 65 wt. %, 15 wt. % to 55 wt. %, 25 wt. % to 45 wt. %, or 30 wt. % to 40 wt. %. In some implementations, the amount of salicin is about 30 wt. %.

In some implementations of the composition, for example, in a composition including ginger root, L-Theanine, caffeine, and salicin, the amount of ginger root can be 40 wt. % to 80 wt. %, 50 wt. % to 70 wt. %, or 55 wt. % to 60 wt. % (e.g., 57 wt. %), the amount of L-Theanine can be 2.5 wt. % to 15 wt. %, 5 wt. % to 10 wt. %, 5 wt. % to 7 wt. %, or 7.5 wt. % to 12.5 wt. % (e.g., 6 wt. % or 10 wt. %), the amount of caffeine can be 1 wt. % to 10 wt. %, 1 wt. % to 5 wt. %, or 5 wt. % to 10 wt. % (e.g., 3 wt. % or 8 wt. %), and the amount of salicin can be 10 wt. % to 50 wt. %, 20 wt. % to 40 wt. %, or 20 wt. % to 30 wt. %. In some implementations, a ratio of caffeine to salicin is about 1:10, a ratio of caffeine to ginger is about 1:20, and a ratio of caffeine to L-Theanine is about 1:2. In some implementations, a ratio of ginger to L-Theanine is in a range of 1:5 to 1:15, a ratio of ginger to caffeine is in a range of 1:2 to 1:100, and a ratio of ginger to salicin is in a range of 1:1 to 1:3.

In an example of a capsule containing a 580 mg dose of the exemplary composition, the capsule can contain 333 mg of ginger root, 33 mg of L-Theanine, 17 mg of caffeine, and 167 mg of salicin, e.g., with the remaining mass including optional active ingredients (e.g., vitamins and/or electrolytes) or inactive substances. In another example of a capsule containing a 1740 mg dose of the exemplary composition, the capsule can contain 1000 mg of ginger root, 100 mg of L-Theanine, 50 mg of caffeine, and 500 mg of salicin, e.g., with the remaining mass including optional active ingredients or inactive substances. In some implementations of the exemplary composition, for example, three 00size gelatin capsules each containing 30 mg of ginger root, 33 mg of L-Theanine, 17 mg of caffeine, and 167 mg of salicin may constitute a single dose of the composition.

In some embodiments of the composition, for example, the composition (including ginger, L-Theanine, and caffeine or including ginger, L-Theanine, caffeine, and salicin) can further include peppermint oil. Peppermint oil is an herbal extract made from the essential oils of peppermint leaves. Peppermint is understood to alleviate nausea, headache, and/or fatigue. In some implementations of the composition, for example, the peppermint oil can be included in an amount of at least 140 mg, at least 160 mg, or at least 180 mg. In some implementations of the composition, for example, the amount of peppermint oil can be in a range 140 mg to 220 mg, 160 mg to 200 mg, or 170 mg to 190 mg. In some implementations, for example, the amount of peppermint oil is 180 mg (e.g., per single dose). In some implementations, for example, the amount of peppermint oil in the composition can be 5 wt. % to 15 wt. % or 7.5 wt. % to 12.5 wt. %. In some implementations, the amount of peppermint oil is 10 wt. %. In some implementations, a ratio of ginger to L-Theanine is in a range of 1:5 to 1:15, a ratio of ginger to caffeine is in a range of 1:2 to 1:100, and a ratio of ginger to peppermint oil is in a range of 1:2 to 1:20. In some implementations, a ratio of ginger to L-Theanine is in a range of 1:5 to 1:15, a ratio of ginger to caffeine is in a range of 1:2 to 1:100, a ratio of ginger to salicin is in a range of 1:1 to 1:3, and a ratio of ginger to peppermint oil is in a range of 1:2 to 1:20.

In some embodiments of the composition, for example, the composition (including ginger, L-Theanine, and caffeine or including ginger, L-Theanine, caffeine, and salicin) can further include vitamin B complex (e.g., vitamins B1, B2, B3, B5, B6, B7, B9, and B12, or combinations thereof) to replenish vitamins lost through drinking alcohol (e.g., vitamins consumed in the alcohol breakdown process in the liver) and to combat headaches associated with the body's processing of alcohol, i.e., the eighth and fifth physiological factors discussed above. In some implementations, the vitamin B complex includes vitamins B1, B6, and B12. In some implementations of the composition, for example, the amount of vitamin B complex or blend can be in a range 1 mg to 50 mg, 1 mg to 5 mg, 10 mg to 50 mg, 20 mg to 50 mg, 30 mg to 50 mg, or 40 mg to 50 mg. In some implementations, for example, the composition can include additional vitamins, e.g., including vitamin C and vitamin E. In some implementations of the composition, for example, the vitamin C can be included in an amount of at least 5 mg, at least 10 mg, at least 20 mg, at least 30 mg, at least 40 mg, at least 50 mg, at least 60 mg, at least 70 mg, or at least 80 mg. In some implementations of the composition, for example, the amount of vitamin C can be in a range 5 mg to 500 mg, 10 mg to 400 mg, 20 mg to 300 mg, 30 mg to 250 mg, 40 mg to 200 mg, 50 mg to 200 mg, 50 mg to 150 mg, 50 mg to 100 mg, or 75 mg to 100 mg. In some implementations of the composition, for example, the vitamin E can be included in an amount of at least 15 international unit (IU) (e.g., one IU of Vitamin D d-alpha-Tocopherol succinate equals to 0.83 mg). In some implementations of the composition, for example, the amount of vitamin E can be in a range 10 IU and 25 IU, 15 IU and 25 IU, or 15 IU and 20 IU. In some implementations, a ratio of ginger to L-Theanine is in a range of 1:5 to 1:15, a ratio of ginger to caffeine is in a range of 1:2 to 1:100, and a ratio of ginger to a vitamin complex (e.g., one or more vitamin B including but not limited to vitamin B1, B6, and/or B12; vitamin C; and/or vitamin E) is in a range of 1:5 to 1:20. In some implementations, a ratio of ginger to L-Theanine is in a range of 1:5 to 1:15, a ratio of ginger to caffeine is in a range of 1:2 to 1:100, a ratio of ginger to salicin is in a range of 1:1 to 1:3, and a ratio of ginger to a vitamin complex (e.g., one or more vitamin B including but not limited to vitamin B1, B6, and/or B12; vitamin C; and/or vitamin E) is in a range of 1:5 to 1:20.

In some embodiments of the composition, for example, the composition (including ginger, L-Theanine, and caffeine or including ginger, L-Theanine, caffeine, and salicin) further includes electrolytes and salts in various forms to combat dehydration and electrolyte imbalances and headaches associated with the body processing alcohol, i.e., the first and fifth physiological factors discussed above. For example, electrolytes can include a mixture of some or all of the following exemplary electrolytes in their various forms: sodium, potassium, chloride, calcium, magnesium, bicarbonate, phosphate, and sulfate. For example, the salts can include sodium chloride (NaCl), potassium chloride (KCl), or other salts. In some implementations of the composition, for example, the electrolytes complex or blend mixture can be included in an amount of at least 20 mg or at least 30 mg. In some implementations of the composition, for example, the amount of Na and/or K in the electrolytes complex or blend mixture can be in a range 20 mg to 40 mg or 25 mg to 35 mg. In some implementations, for example, the amount of Na or K can be 30 mg (e.g., 15 mg of Na and 15 mg of K electrolytes). In some implementations, a ratio of ginger to L-Theanine is in a range of 1:5 to 1:15, a ratio of ginger to caffeine is in a range of 1:2 to 1:100, and a ratio of ginger to one or more electrolytes is in a range of 1:10 to 1:500. In some implementations, a ratio of ginger to L-Theanine is in a range of 1:5 to 1:15, a ratio of ginger to caffeine is in a range of 1:2 to 1:100, a ratio of ginger to salicin is in a range of 1:1 to 1:3, and a ratio of ginger to one or more electrolytes is in a range of 1:10 to 1:500. In some implementations, a ratio of ginger to L-Theanine is in a range of 1:5 to 1:15, a ratio of ginger to caffeine is in a range of 1:2 to 1:100, a ratio of ginger to salicin is in a range of 1:1 to 1:3, a ratio of ginger to a vitamin complex (e.g., one or more vitamin B including but not limited to vitamin B1, B6, and/or B12; vitamin C; and/or vitamin E) is in a range of 1:5 to 1:20, and a ratio of ginger to one or more electrolytes is in a range of 1:10 to 1:500.

In some embodiments of the composition, for example, the composition can further include sugars or carbohydrates in their various forms (e.g., such as glucose, dextrose, fructose, etc.) for the purpose of combating low blood sugar and headaches associated with the body processing alcohol after responsible alcohol consumption, e.g., the third and fifth physiological factors discussed above.

In some implementations of an exemplary composition including ginger root, L-Theanine, caffeine, salicin, and vitamins, for example, the amount of the constituents can be as follows: ginger root can be 40 wt. % to 80 wt. %, 50 wt. % to 70 wt. %, or 55 wt. % to 60 wt. % (e.g., about 57 wt. %), L-Theanine can be 2.5 wt. % to 15 wt. %, 5 wt. % to 10 wt. %, 5 wt. % to 7 wt. %, or 7.5 wt. % to 12.5 wt. % (e.g., about 6 wt. %), caffeine can be 1 wt. % to 10 wt. %, 1 wt. % to 5 wt. %, or 5 wt. % to 10 wt. % (e.g., about 3 wt. %), salicin can be 10 wt. % to 50 wt. %, 20 wt. % to 40 wt. %, or 20 wt. % to 30 wt. % (e.g., about 29 wt. %), and vitamins can be 1 wt. % to 10 wt. %, 2 wt. % to 8 wt. %, 3 wt. % to 7 wt. %, or 4 wt. % to 6 wt. % (e.g., about 5 wt. %). In some implementations of the compositions, the vitamins can include vitamin C, vitamin B1, vitamin B6, and vitamin B12, and the amount of the constituents can be as follows: vitamin C can be 4 wt. % to 6 wt. % (e.g., about 5 wt. %), vitamin B1 can be 0.05 wt. % to 0.1 wt. % (e.g., about 0.07 wt. %), vitamin B6 can be 1 wt. % to 2 wt. % (e.g., about 1.7 wt. %), and vitamin B12 can be below 0.01%. In an example of a capsule containing a 580 mg dose of the exemplary composition, the capsule can contain 333 mg of ginger root, 33 mg of L-Theanine, 17 mg of caffeine, 167 mg of salicin, 90 mg of vitamin C, 1.2 mg of vitamin B1, 1.7 mg of vitamin B6, and 0.002 mg of vitamin B12.

In some embodiments of the composition, for example, the composition can further include cannabidiol (CBD) ($C_{21}H_{30}O_2$). CBD is a type of cannabinoid extracted from cannabis plants. In some implementations, the CBD is derived from hemp plant. CBD is understood to cause feelings of relaxation, pain relief, and appetite stimulation, which can alleviate adverse effects of responsible alcohol consumption. Moreover, CBD is understood to modulate the inflammatory process in the liver and may reduce alcohol-induced liver steatosis (increased fat in the liver) and fibrosis (excessive accumulation of extracellular matrix (ECM) proteins in liver tissue).

In some implementations of the composition, for example, the CBD can be included in an amount of at least 10 mg, at least 15 mg, or at least 20 mg. In some implementations of the composition, for example, the amount of CBD can be in a range 5 mg to 50 mg, 7.5 mg to 40 mg, 10 mg to 30 mg, 20 mg to 30 mg, or 20 mg to 25 mg. In some implementations, for example, the amount of CBD is 23 mg (e.g., per single dose, which can be distributed in one or more composition delivery units like a capsule, tablet, liquid, powder, gummy, etc.). In some implementations, for example, the amount of CBD in the composition can be 0.5 wt. % to 4 wt. %, 1 wt. % to 4 wt. %, or 1 wt. % to 2 wt. %. In some implementations, the amount of CBD is 1.3 wt. %.

In some implementations of the composition, for example, in a composition including ginger root, L-Theanine, caffeine, and CBD, the amount of ginger (e.g., from ginger root) can be 30 wt. % to 85 wt. %, 40 wt. % to 80 wt. %, 50 wt. % to 70 wt. %, or 55 wt. % to 60 wt. % (e.g., about 67.7 wt. % or about 67 wt. % to 68 wt. %), the amount of L-Theanine can be 2.5 wt. % to 15 wt. %, 5 wt. % to 10 wt. %, 5 wt. % to 7 wt. %, or 7.5 wt. % to 12.5 wt. % (e.g., about 11 wt. % or about 10 wt. % to 12 wt. %), the amount of caffeine can be 1 wt. % to 10 wt. %, 1 wt. % to 5 wt. %, or 5 wt. % to 10 wt. % (e.g., about 8.8 wt. % or about 8 wt. % to 9 wt %), and the amount of CBD can be 0.1 wt. % to 10 wt. %, 0.5 wt. % to 4 wt. %, 1 wt. % to 4 wt. %, or 1 wt. % to 2 wt. % (e.g., about 1.5 wt. % or about 1 wt. % to 2 wt. %). In some implementations, a ratio of CBD to caffeine is about 6:1, a ratio of CBD to ginger root is about 43:1, and a ratio of CBD to L-Theanine is about 7:1. In some implementations, a ratio of ginger to L-Theanine is in a range of 1:3 to 1:15, a ratio of ginger to caffeine is in a range of 1:2 to 1:100, and a ratio of ginger to CBD is in a range of 1:10 to 1:500.

In an example of a capsule containing a 551 mg dose of the exemplary composition, the capsule can contain 333 mg of ginger root, 54 mg of L-Theanine, 43 mg of caffeine, and 7.7 mg of CBD. In another example of a capsule containing a 1656 mg dose of the exemplary composition, the capsule can contain 1000 mg of ginger root, 162 mg of L-Theanine, 130 mg of caffeine, and 23 mg of CBD. In some implementations of the exemplary composition, for example, three 00size gelatin capsules each containing 333 mg of ginger root, 54 mg of L-Theanine, 43 mg of caffeine, and 7.7 mg of CBD may constitute a single dose of the composition.

In some implementations of the composition, for example, in a composition including ginger root, L-Theanine, caffeine, CBD, and peppermint oil, the amount of ginger (e.g., from ginger root) can be 30 wt. % to 85 wt. %, 40 wt. % to 80 wt. %, 50 wt. % to 70 wt. %, or 55 wt. % to 60 wt. % (e.g., about 60.4 wt. % or about 60 wt. % to 61 wt. %), the amount of L-Theanine can be 2.5 wt. % to 15 wt. %, 5 wt. % to 10 wt. %, 5 wt. % to 7 wt. %, or 7.5 wt. % to 12.5 wt. % (e.g., about 9.8 wt. % or about 9 wt. % to 10 wt. %), the amount of caffeine can be 1 wt. % to 10 wt. %, 1 wt. % to 5 wt. %, or 5 wt. % to 10 wt. % (e.g., about 7.8 wt. % or about 7 wt. % to 8 wt. %), the amount of CBD can be 0.5 wt. % to 4 wt. %, 1 wt. % to 4 wt. %, or 1 wt. % to 2 wt. % (e.g., about 1.3 wt. % or about 1 wt. % to 2 wt. %), and the amount of peppermint oil in the composition can be 5 wt. % to 15 wt. % or 7.5 wt. % to 12.5 wt. % (e.g., about 10.8 wt. % or about 10 wt. % to 11 wt. %). In some implementations, a ratio of ginger to L-Theanine is in a range of 1:3 to 1:15, a ratio of ginger to caffeine is in a range of 1:2 to 1:100, a ratio of ginger to CBD is in a range of 1:10 to 1:100, and a ratio of ginger to peppermint oil is in a range of 1:3 to 1:12.

In an example of a capsule containing a 551 mg dose of the exemplary composition, the capsule can contain 333 mg of ginger root, 54 mg of L-Theanine, 43 mg of caffeine, 7.7 mg of CBD, and 60 mg of peppermint oil. In another example of a capsule containing a 1656 mg dose of the exemplary composition, the capsule can contain 1000 mg of ginger root, 162 mg of L-Theanine, 130 mg of caffeine, 23 mg of CBD, and 180 mg of peppermint oil. In some implementations of the exemplary composition, for example, three 00size gelatin capsules each containing 333 mg of ginger root, 54 mg of L-Theanine, 43 mg of caffeine, 7.7 mg of CBD, and 60 mg of peppermint oil may constitute a single dose of the composition.

In some implementations of an exemplary composition including ginger (e.g., from ginger root), L-Theanine, caffeine, CBD, peppermint oil, and at one or more of at least one vitamin and/or at least one electrolyte, for example, the amount of the constituents can be as follows: ginger root can be 30 wt. % to 85 wt. %, 40 wt. % to 80 wt. %, 50 wt. % to 70 wt. %, or 55 wt. % to 60 wt. % (e.g., about 60 wt. %), L-Theanine can be 2.5 wt. % to 15 wt. %, 5 wt. % to 10 wt. %, 5 wt. % to 7 wt. %, or 7.5 wt. % to 12.5 wt. % (e.g., about 10 wt. %), caffeine can be 1 wt. % to 10 wt. %, 1 wt. % to 5 wt. %, or 5 wt. % to 10 wt. % (e.g., about 8 wt. %), CBD can be 0.5 wt. % to 4 wt. %, 1 wt. % to 4 wt. %, or 1 wt. % to 2 wt. % (e.g., about 1.3 wt. %), peppermint oil can be 5 wt. % to 15 wt. % or 7.5 wt. % to 12.5 wt. % (e.g., 10 wt. %), vitamins (e.g., one or more of vitamin B1, B6, B12, C, and/or E) can be 5 wt. % to 10 wt. %, 4 wt. % to 9 wt. %, or 5 wt. % to 8 wt. % (e.g., about 7.9 wt. %), and electrolytes (e.g., Na and K) can be 5 wt. % to 15 wt. % (e.g., about 2 wt. %). In some implementations of the compositions, the vitamins can include vitamin C, vitamin E, vitamin B1, vitamin B6, and vitamin B12, and the amount of the constituents can be as follows: vitamin C can be 4 wt. % to 6 wt. % (e.g., about 4.5 wt. %), vitamin E can be 0.5 wt. % to 1.5 wt. % (e.g., about 0.9 wt. %), vitamin B1 can be 0.5 wt. % to 1.5 wt. % (e.g., about 1.2 wt. %), vitamin B6 can be 0.5 wt. % to 1.5 wt. % (e.g., about 1.2 wt. %), and vitamin B12 can be below 0.01%. In an example of a capsule containing a 550 mg dose of the exemplary composition, the capsule can contain 333 mg of ginger root, 54 mg of L-Theanine, 43 mg of caffeine, 7.7 mg of CBD, 60 mg of peppermint oil, 25 mg of vitamin C, 6.7 mg of vitamin B1, 6.7 mg of vitamin B6, 0.003 mg of vitamin B12, 5 mg of Na, and 5 mg of K. In some implementations, a ratio of ginger to L-Theanine is in a range of 1:3 to 1:15, a ratio of ginger to caffeine is in a range of 1:2 to 1:100, a ratio of ginger to CBD is in a range of 1:10 to 1:100, a ratio of ginger to peppermint oil is in a range of 1:3 to 1:12, a ratio of ginger to a vitamin complex (e.g., one or more vitamin B including but not limited to vitamin B1, B6, and/or B12; vitamin C; and/or vitamin E) is in a range of 1:3 to 1:20, and a ratio of ginger to one or more electrolytes is in a range of 1:10 to 1:500.

It should be noted that the exemplary embodiments of the disclosed technology include various formulations made from any of the above-mentioned or below-mentioned compositions.

For example, the disclosed compositions include formulations of ingredients capable of effectively and comprehensively treating multiple discomforting symptoms of responsible alcohol consumption and the negative effects of alcohol on the body (e.g., liver health, brain and nervous system health, and gastrointestinal health). In some implementations, for example, compositions of the present technology can be used as a daily supplement by individuals, e.g., which can aid in the replenishing of nutrients, vitamins, and electrolytes of the individual and/or reverse negative effects on physiological function. In some implementations, for example, a composition of the disclosed technology can be used after the responsible use of alcohol. For example, an exemplary composition could be taken one to twelve hours after responsible alcohol consumption or soon after feeling physical symptoms associated with responsible alcohol consumption, as noted above. For example, an exemplary composition could be taken shortly after waking up (e.g., the next morning) after responsible alcohol consumption the previous evening.

The disclosed compositions can be contained in the form of capsules, tablets, gummies, lozenges, etc. or extended-release capsules or tablets or other composition delivery unit. In some implementations, for example, a composition of the disclosed technology can be contained in a liquid delivery mechanism, e.g., such that the exemplary composition was produced in the form of a drink (e.g., soft drink). In some implementations, for example, a composition of the disclosed technology can be made in the form of a liquid concentrate or shot which could be taken alone or added to water or a drink. In some implementations, for example, a composition of the disclosed technology can be made in the form of powder in a packet, e.g., the contents of which may be dispersed into water or a drink. The disclosed compositions can be used for relief from single or multiple exhibited symptoms suffered after responsible drinking in any of the above delivery forms (e.g., a pill, drink, liquid concentrate, packet of powder, gummy, chewable tablet, gum, lozenges, infused food, and/or other solid form). In some implementations, for example, the disclosed compositions can be used as a daily supplement to aid in general health.

For example, administering the disclosed compositions in certain amounts and/or concentrations can treat or alleviate discomforting symptoms after the onset of such symptoms perceived by the consumer. In implementations, for example, the exemplary embodiments of the disclosed compositions can be administered in the form of example forms mentioned above (e.g., pills, drinks, liquid concentrates, packets of powder, gummy, chewable tablet, gum, lozenges, infused food, and/or other solid form).

Figure 1:
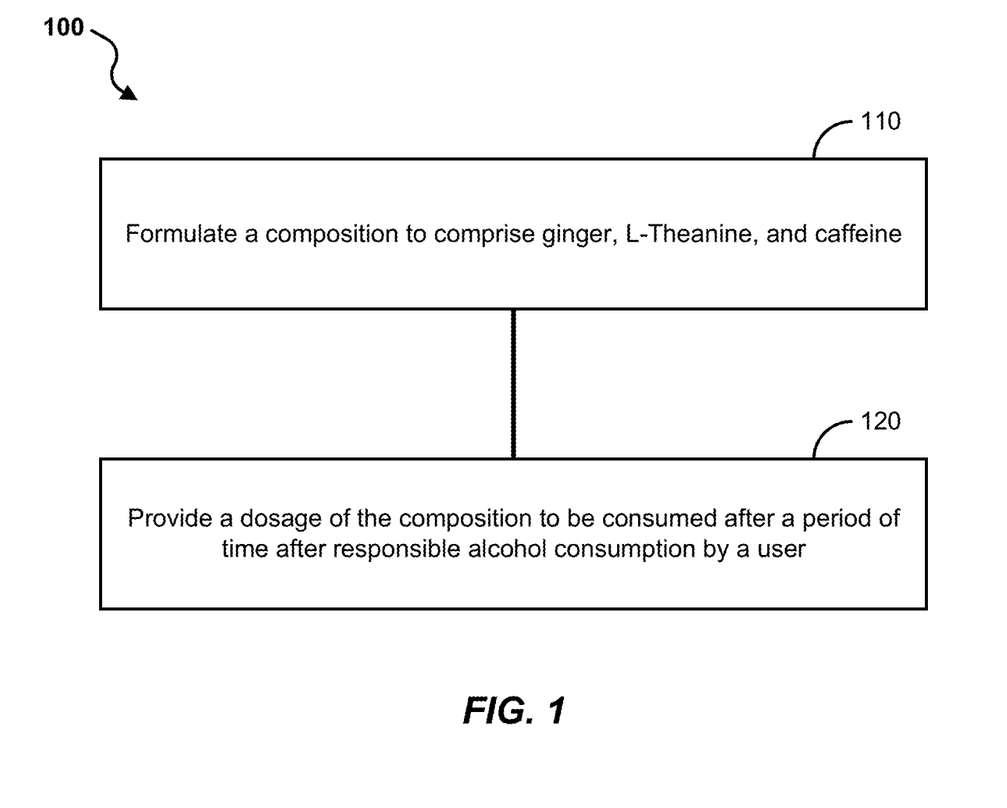
FIG. 1 shows a diagram of an exemplary method for mitigating adverse effects of responsible alcohol consumption using a composition in accordance with the disclosed technology.

FIG. 1 shows a diagram of an exemplary method 100 for mitigating adverse effects of responsible alcohol consumption using example embodiments of a composition in accordance with the disclosed technology. In some embodiments, for example, the method 100 for mitigating adverse effects of responsible alcohol consumption includes a process 110 to formulate a composition for mitigating adverse effects of responsible alcohol consumption in a person to comprise at least ginger (e.g., from ginger root), L-Theanine (e.g., from White Willow (*Salix alba*) Bark Extract), and caffeine (e.g., from Green Tea (*Camellia sinensis*) (leaf) Extract); and a process 120 to provide a dose of the composition to a user after a period of time after responsible alcohol consumption by the user. In some implementations of the method 100, for example, the dose includes multiple capsules (e.g., three capsules). In some implementations of the method 100, for example, the dose includes about 1000 mg of ginger (e.g., from ginger root), about 100 mg of L-Theanine (e.g., from Green Tea (leaf) Extract), and about 50 mg of caffeine (e.g., from Green Tea (leaf) Extract), which may optionally include other active ingredients or inactive substances. In some implementations of the method 100, for example, the dose includes about 1000 mg of ginger (e.g., from ginger root), about 100 mg of L-Theanine (e.g., from Green Tea (leaf) Extract), about 50 mg of caffeine (e.g., from Green Tea (leaf) Extract), and about 500 mg of salicin (e.g., from White Willow (*Salix alba*) Bark Extract), which may optionally include other active ingredients or inactive substances. The period of time after responsible alcohol consumption can be at least 2 hours or 3 hours or 4 hours or 5 hours or 6 hours or 7 hours or 8 hours or 9 hours or 10 hours or 11 hours or 12 hours after the consumption of alcohol. For example, the composition of the present technology is provided in the morning when the user has consumed alcohol the night before.

EXAMPLE IMPLEMENTATIONS

Example implementations of an example embodiment of the composition was performed, which demonstrated the composition was effective in reducing adverse effects of alcohol responsibly consumed by subjects when the composition was ingested at least four hours after the last instance of consumption of an alcoholic beverage. The example embodiment of the composition included ginger from ginger root extract (e.g., 1000 mg), salicin from white willow bark extract (e.g., 500 mg), L-Theanine (e.g., 100 mg), and caffeine from green tea leaf extract (e.g., 50 mg), and was formed in one or more vegetable-based capsules (e.g., Hypromellose capsule). The example implementation included ten subjects that willingly agreed to follow protocols of the study. Each subject responsibly consumed one or more alcoholic beverages during an evening, prior to sleep, that each respective subject knew (based on their own self knowledge and experience) would likely cause head discomfort, fatigue, drowsiness, nausea, or other inconvenient symptoms the following morning. Eight of the ten subjects reported to experience the anticipated symptoms and took the exemplary composition (e.g., ingested the capsule(s)). The eight subjects recorded a normalized score based on their perceived symptoms each 20 minutes over the course of four hours after taking the composition. At time=0 hr (i.e., the time of ingestion of the capsule(s)), each subject's normalized symptoms were assigned a score of 10 associated with the height of their symptoms. For every 20 minutes thereafter over the four-hour period, each subject reported their perceived symptoms on a scale of 0 to 10 (with 0 being no symptoms and 10 being the original symptoms), according to the protocol.

Figure 2:
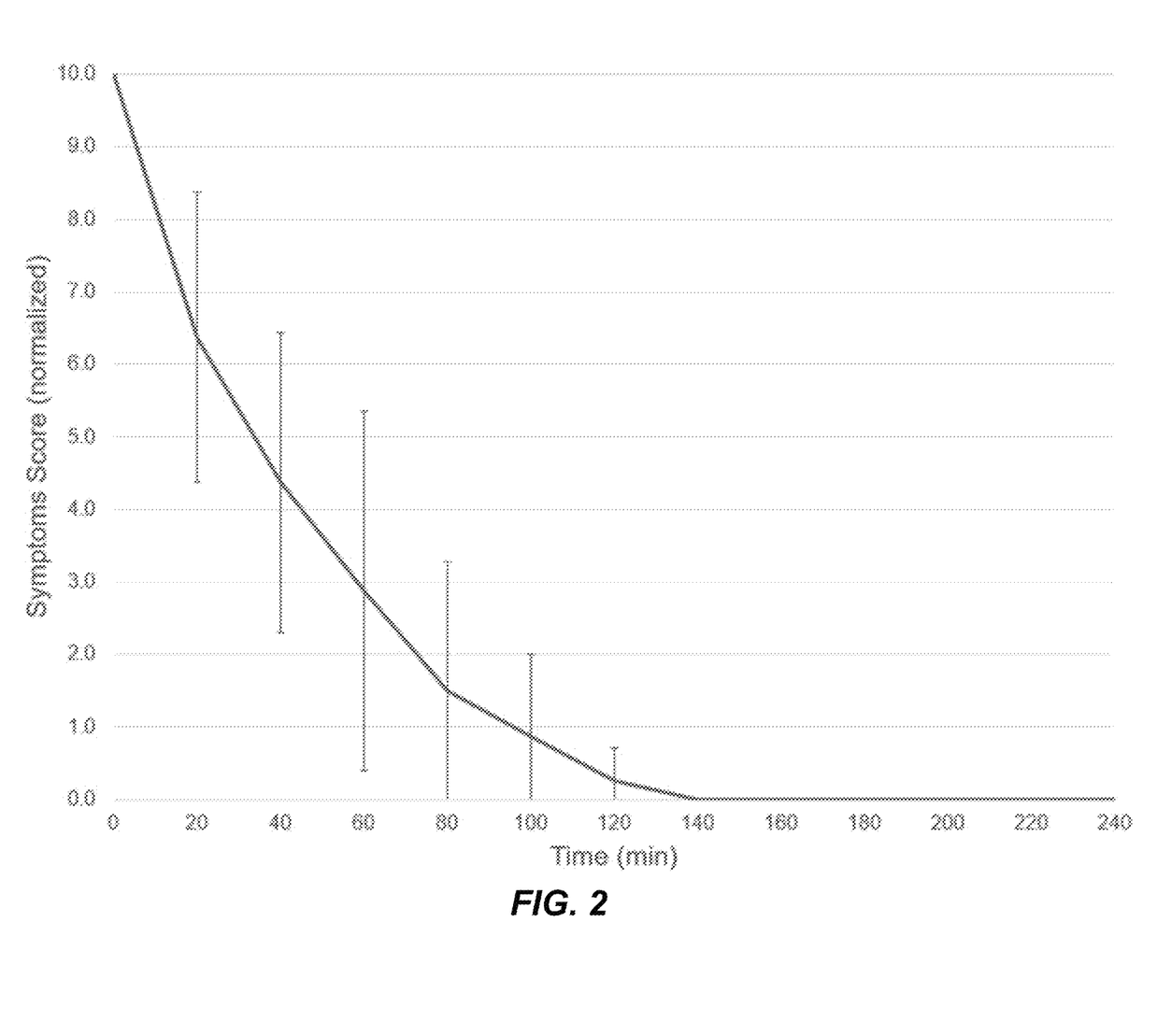
FIG. 2 shows a data plot depicting results of an example implementation for subjects using an example embodiment of a composition in accordance with the present technology that reduced adverse symptoms due to alcohol responsibly consumed.

FIG. 2 shows a data plot depicting the results of the example implementation for subjects using the example embodiment of the composition to reduce adverse effects of alcohol the subjects responsibly consumed. As shown in the data plot, the subjects experienced a substantial reduction in their perceived discomforting symptoms associated with their responsible consumption of alcohol from the previous evening. The average reduction in the subjects' perceived symptoms dropped by 36% within the first 20 minutes, followed by a further reduction by another 20% (i.e., 56% reduction from the original symptoms) for the next 20 minutes, and followed by a further reduction by another 15% for the next 20 minutes, thereby resulting in an average 71% reduction within the first hour after consuming the composition. By the second hour after consuming the composition, the average reduction in the subjects' perceived discomforting symptoms was over 97%, e.g., indicating an effectively full recovery from the symptoms. None of the subjects reported to experience discomforting symptoms at or after 140 minutes, as shown in Table 1.

TABLE 1

| Time (min) | 0 | 20 | 40 | 60 | 80 | 100 | 120 | 140 | 160 | 180 | 200 | 220 | 240 |
|---|---|---|---|---|---|---|---|---|---|---|---|---|---|
| Avg. | 10.0 | 6.4 | 4.4 | 2.9 | 1.5 | 0.9 | 0.3 | 0.0 | 0.0 | 0.0 | 0.0 | 0.0 | 0.0 |
| St. Dev. | 0.0 | 2.0 | 2.1 | 2.5 | 1.8 | 1.1 | 0.5 | 0.0 | 0.0 | 0.0 | 0.0 | 0.0 | 0.0 |

Another example implementation of the example embodiment of the composition used in FIG. 2 was performed, which further demonstrated the composition was effective in reducing adverse effects of alcohol responsibly consumed by subjects. The additional study included seven subjects that willingly agreed to follow protocols of the study by drinking one or more standard alcoholic drinks (e.g., 14 g of ethanol) a night before taking one dose of the composition the following morning, i.e., with at least six hours of sleep between the last consumed drink and the ingestion of the composition. The composition ingested comprised ginger from ginger root extract (e.g., 1000 mg), salicin from white willow bark extract (e.g., 500 mg), L-Theanine (e.g., 100 mg), and caffeine from green tea leaf extract (e.g., 50 mg)). Later the day of the dose of the composition was taken, the subjects were asked to complete a questionnaire about their perceived symptoms before and after the dose was taken. Subjects were asked about their perceived feelings about their (i) head, (ii) stomach, (iii) queasiness, (iv) energy level, and (v) overall wellbeing from before and after the composition dose, which they rated on a scale of 1 to 10 (with 1 feeling the worst and 10 feeling well/normal).

Figure 3:
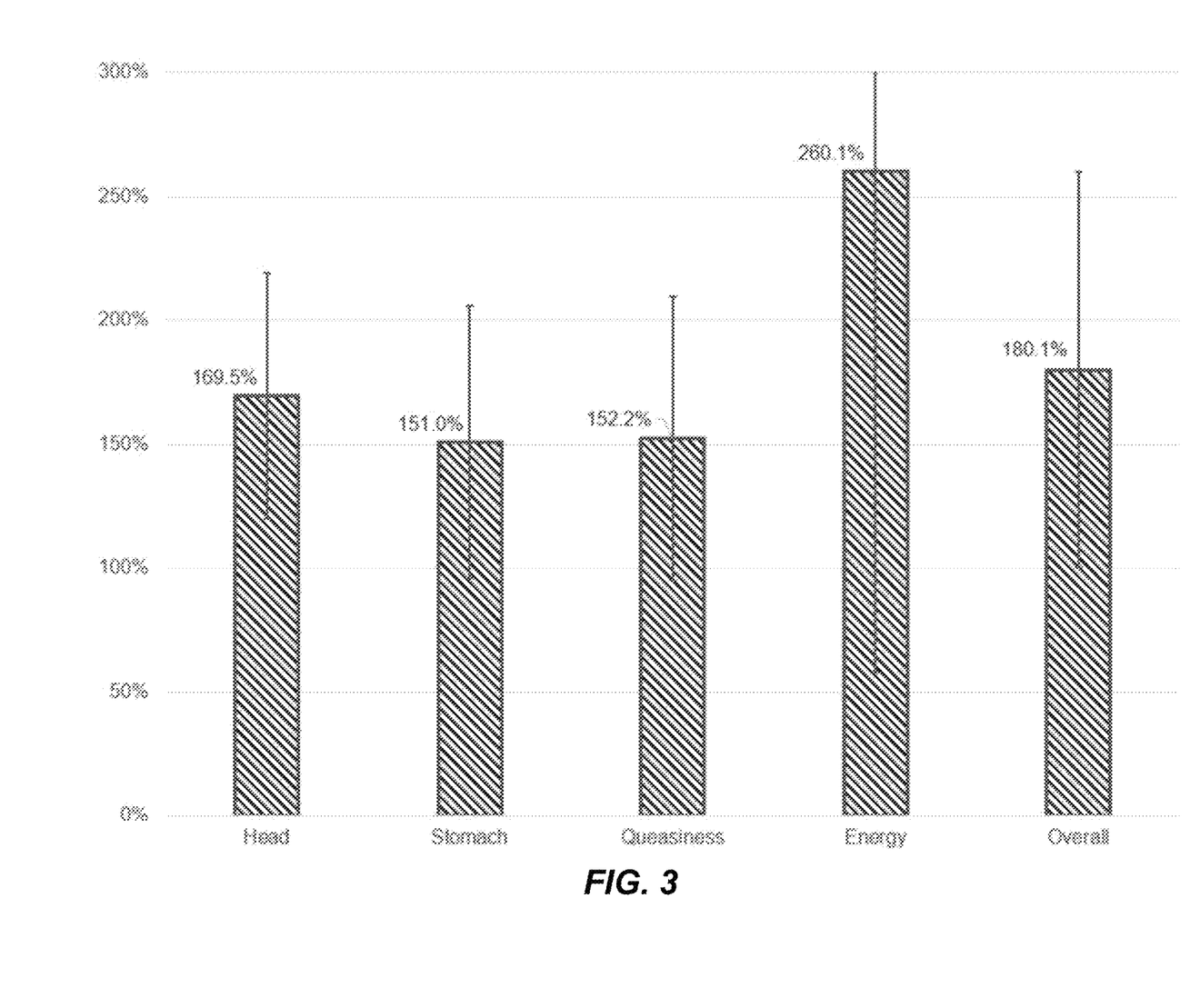
FIG. 3 shows a data plot depicting example response results to questions about perceived symptoms of responsible alcohol consumption by subjects who used an example embodiment of a composition to reduce adverse effects of alcohol, in accordance with the present technology.

FIG. 3 shows a data plot depicting the response results by the subjects who participated in the additional example implementation using the example embodiment of the composition to reduce adverse effects of alcohol the subjects responsibly consumed. As shown in the data plot, the subjects reported an average 150% or greater improvement to their initial feelings for the respective symptom, body region, or condition, i.e., their head, stomach, queasiness, energy, and overall wellbeing, after taking the dose of the composition.

Subjects were also asked how long it took for them to begin feeling a positive effect after taking the dose of the composition. Table 2 shows the subjects' responses, which demonstrate the average time for the composition to begin affecting them in feeling better was 32.1 minutes, with a standard deviation of 15.2 minutes.

TABLE 2

| Subject | 1 | 2 | 3 | 4 | 5 | 6 | 7 |
|---|---|---|---|---|---|---|---|
| Time (min) | 30 | 45 | 30 | 60 | 20 | 20 | 20 |

EXAMPLES

The following examples are illustrative of several embodiments of the present technology. Other exemplary embodiments of the present technology may be presented prior to the following listed examples, or after the following listed examples.

In an example of the present technology (example 1), a composition for mitigating adverse effects of alcohol includes ginger root; L-Theanine; and caffeine.

Example 2 includes the composition in example 1 or any of examples 1-15, in which the composition includes 40 wt. % to 80 wt. % of the ginger root, 2.5 wt. % to 15 wt. % of the L-Theanine, and 1 wt. % to 10 wt. % of the caffeine.

Example 3 includes the composition in example 1 or any of examples 1-15, in which the composition includes the ginger root includes an amount of 100 mg to 2000 mg, the L-Theanine includes an amount of 10 mg to 400 mg, and the caffeine includes an amount 10 mg to 300 mg.

Example 4 includes the composition in example 1 or any of examples 1-15, where the composition further includes salicin.

Example 5 includes the composition in example 4 or any of examples 1-15, in which the salicin is included in white willow bark extract.

Example 6 includes the composition in example 4 or any of examples 1-15, in which the composition 40 wt. % to 80 wt. % of the ginger root, 2.5 wt. % to 15 wt. % of the L-Theanine, 1 wt. % to 10 wt. % of the caffeine, and 10 wt. % to 50 wt. % of the salicin.

Example 7 includes the composition in example 1 or any of examples 1-15, in which the composition includes the ginger root in an amount of 100 mg to 2000 mg, the L-Theanine in an amount of 10 mg to 400 mg, the caffeine in an amount of 10 mg to 300 mg, and the salicin in an amount of 50 mg to 3000 mg.

Example 8 includes the composition in example 1 or any of examples 1-15, further including one or more of vitamin C, vitamin E, vitamin B1, vitamin B6, and vitamin B12.

Example 9 includes the composition in example 8 or any of examples 1-15, composition includes 40 wt. % to 80 wt. % of the ginger root, 2.5 wt. % to 15 wt. % of the L-Theanine, 1 wt. % to 10 wt. % of the caffeine, 4 wt. % to 6 wt. % of vitamin C, 0.05 wt. % to 0.1 wt. % of vitamin B1, 1 wt. % to 2 wt. % of vitamin B6, and below 0.01 of vitamin B12%.

Example 10 includes the composition of example 8 or any of examples 1-15, the ginger root includes an amount of 100 mg to 2000 mg, the L-Theanine includes an amount of 10 mg to 400 mg, the caffeine includes an amount of 10 mg to 300 mg, and the one or more of vitamin C, vitamin E, vitamin B1, vitamin B6, and vitamin B12 includes an amount of 5 mg to 550 mg.

Example 11 includes the composition of example 1 or any of examples 1-15, in which the caffeine is a natural caffeine extract from green tea.

Example 12 includes the composition of example 1 or any of examples 1-15, in which the ginger root is extracted from ginger root extract.

Example 13 includes the composition of example 1 or any of examples 1-15, the composition is contained in a capsule, a tablet, a liquid concentrate, a liquid drink, a powder, a gummy, a chewable tablet, a lozenge, or infused food.

Example 14 includes the composition of example 1 or any of examples 1-15, in which the composition further includes one or more of sodium and potassium.

Example 15 includes the composition of example 1 or any of examples 1-15, including peppermint oil.

In an example of the present technology (example 16), a composition for mitigating adverse effects of alcohol includes ginger root; L-Theanine; caffeine; and salicin.

Example 17 includes the composition of example 16 or any of examples 16-19, in which the salicin is included in white willow bark extract.

Example 18 includes the composition of example 16 or any of examples 16-19, in which the composition includes 40 wt. % to 80 wt. % of the ginger root, 2.5 wt. % to 15 wt. % of the L-Theanine, 1 wt. % to 10 wt. % of the caffeine, and 10 wt. % to 50 wt. % of the salicin.

Example 19 includes the composition of example 16 or any of examples 16-19, in which the ginger root includes an amount of at least 100 mg, the L-Theanine includes an amount of 10 mg to 400 mg, the caffeine includes an amount of 10 mg to 300 mg, and the salicin includes an amount of 50 mg to 3000 mg.

In an example of the present technology (example 20), a method of mitigating adverse effects of responsible alcohol consumption. The method includes providing a dosage of a composition to be consumed after a period of time after responsible alcohol consumption by a user, in which the composition is a composition defined by any of the examples 1-19 above or example 20.

In an example of the present technology (example 21), a composition contained in at least one of a capsule, a tablet, a liquid concentrate, a liquid drink, a powder, a gummy, a chewable tablet, a gum, a lozenge, or an infused food as in any of examples 1-19 or as described in this patent document.

CONCLUSION

The term "about," as used herein when referring to a measurable value such as an amount or concentration and the like, may encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A capsule or tablet for mitigating adverse effects of alcohol, consisting essentially of:
    ginger root;
    L-Theanine;
    caffeine;
    salicin;
    at least one of vitamin C or vitamin E; and
    at least one B vitamin.

2. The capsule or tablet of claim 1, wherein the at least one B vitamin includes one or more of vitamin B1, vitamin B6, or vitamin B12.

3. The capsule or tablet of claim 1,
    wherein the capsule or tablet includes 40 wt. % to 80 wt. % of the ginger root, 2.5 wt. % to 15 wt. % of the L-Theanine, 1 wt. % to 10 wt. % of the caffeine, 10 wt. % to 50 wt. % of the salicin, and 1 wt. % to 10 wt. % of the at least one of the vitamin C or the vitamin E and the at least one B vitamin.

4. The capsule or tablet of claim 1,
    wherein the ginger root includes an amount of at least 100 mg, wherein the L-Theanine includes an amount of 10 mg to 400 mg, wherein the caffeine includes an amount of 10 mg to 300 mg, wherein the salicin includes an amount of 50 mg to 3000 mg, and wherein the at least one of the vitamin C or the vitamin E and the at least one B vitamin includes an amount of 1 mg to 500 mg.

5. The capsule or tablet of claim 1,
    wherein a ratio of the ginger root to the L-Theanine is in a range of 1:5 to 1:15, a ratio of the ginger root to the caffeine is in a range of 1:2 to 1:100, a ratio of the ginger root to the salicin is in a range of 1:1 to 1:3, and a ratio of the ginger root to the one or more of vitamin C, vitamin E, vitamin B1, vitamin B6, or vitamin B12 is in a range of 1:5 to 1:20.

* * * * *